United States Patent

Schenkel

[11] 3,968,210
[45] July 6, 1976

[54] SYNERGISTIC GERMICIDAL COMPOSITIONS CONTAINING 3,5-DIMETHYL-4-CHLOROPHENOL

[75] Inventor: Alan G. Schenkel, High Point, N.C.

[73] Assignee: Ciba-Geigy Corporation, Ardsley, N.Y.

[22] Filed: Aug. 13, 1975

[21] Appl. No.: 604,418

Related U.S. Application Data

[63] Continuation of Ser. No. 370,879, June 18, 1973, abandoned.

[52] U.S. Cl.............................. 424/235; 424/341; 424/347
[51] Int. Cl.² ......................................... A01N 9/02
[58] Field of Search.................. 424/235, 341, 347

[56] References Cited
UNITED STATES PATENTS

| | | |
|---|---|---|
| 3,445,398 | 5/1969 | Jungermann et al. ............. 252/107 |
| 3,506,720 | 4/1970 | Model et al........................ 260/613 |
| 3,629,477 | 12/1971 | Model et al........................ 424/340 |
| 3,800,048 | 3/1974 | Model et al........................ 424/304 |

OTHER PUBLICATIONS

Chemical Abstracts 60:3953b (1964).

*Primary Examiner*—Leonard Schenkman
*Attorney, Agent, or Firm*—Joseph G. Kolodny; Edward McC. Roberts; Probodh I. Almaula

[57] ABSTRACT

A mixture of
 i. 3,5-dimethyl-4-chlorophenol with one of
 ii. bis-(3,5,6-trichloro-2-hydroxyphenyl) methane
 iii. 2,4,4'-trichloro-2'-hydroxydiphenyl ether
 iv. 3,4',5-tribromo salicylanilide
or a mixture of any three of said compounds exhibits synergistic germicidal activity and can be used to provide soaps, detergents and cosmetics with germicidal activity.

9 Claims, No Drawings

SYNERGISTIC GERMICIDAL COMPOSITIONS CONTAINING 3,5-DIMETHYL-4-CHLOROPHENOL

BACKGROUND OF THE INVENTION

This is a cont. Ser. No. 370,879 filed on June 18, 1973, now abandoned.

Investigations by prior artisans have developed substantial numbers of new germicidal agents, particularly for use in various soap, detergent and cosmetic preparations. Many of the germicidal agents, however, have limitations in their use. Some are rendered ineffective in the presence of soap or detergent compositions. Some germicidal agents are effective only against a relatively narrow range of organisms. Certain of the agents are photosensitive and when incorporated into a soap or detergent bar will discolor the bar upon prolonged exposure to sunlight. Some of the compounds suggested by the prior art, although relatively good germicidal agents, do not become truly effective until employed at relatively high levels, for example, up to 2 or 3% by total weight of the detergent product. At high concentrations, one may encounter the problem of skin sensitivity to the germicidal agent. Given the cost of the germicidal agent and the potential problem of sensitivity thereto, it has become desirable to obtain as large a germicidal effect as possible in conjunction with as low a germicidal concentration as possible. Some of these problems have been alleviated by the discovery of the prior art that certain binary combinations of germicidal agents exhibit synergism when admixed and incorporated into soap and detergent formulations and other products. The synergistic combination provides a higher level of germicidal effectiveness for an equal amount of germicidal agent used. This becomes significant because it permits a manufacturer to use a lesser amount of germicidal agent and yet retain a relatively high degree of effectiveness. It should be noted that effective synergistc combinations of germicidal agents are relatively rare and when such combinations are discovered, the synergism is entirely unpredictable. There is, therefore, a continual need for still more effective germicidal agents and combinations of agents having increased substantivity to the skin. Such an agent or mixture of agents can be incorporated into soaps, detergents and cosmetics at lower concentrations than is now practiced to provide an even greater germicidal effectiveness of the product under conventional usage conditions.

SUMMARY OF THE INVENTION

It has now been found that a mixture of
i. 3,5-dimethyl-4-chlorophenol
with one of
ii. bis-(3,5,6-trichloro-2-hydroxyphenyl) methane
iii. 2,4,4'-trichloro-2'-hydroxydiphenyl ether
iv. 3,4',5-tribromo salicylanilide or a mixture of any three of said compounds exhibits synergistic germicidal activity and this activity is maintained when such mixtures are incorporated into various detergent compositions, soaps, combinations thereof or in cosmetic preparations. These compositions possess a high level of germicidal effectiveness over a wide range of organisms, retain their effectiveness in soaps, detergents and cosmetic media and do not have significant discoloration or toxicity problems.

The term "synergistic" and "synergistic composition" as used herein refers to a mixture of two or more discreet agents which, when combined, display a degree of germicidal activity whih is greater than the expected additive germicidal effect of said agents.

As indicated, in one aspect, the invention relates to a binary system comprising a mixture of 3,5-dimethyl-4-chlorophenol with one of bis-(3,5,6-trichloro-2-hydroxyphenyl) methane, 2,4,4'-trichloro-2'-hydroxydiphenyl ether or 3,4',5-tribromo salicylanilide. In another aspect, the invention relates to the discovery that when any three of said compounds are used together, a synergistic germicidal effect is achieved. This has importance in those cases where it is desirable to increase the activity of any one of the components without employing higher concentrations and assumes important economic considerations, since the synergistic effect enables a reduction in total concentration of the germicidal agent, while retaining the desired level of germicidal effect. In another aspect this invention relates to the combination of a binary or ternary synergistic system as described herein with a soap, detergent or cosmetic composition.

The actual mechanism of the potentiating synergistic effect is, at present, indeterminate. However, the invention relates to the synergistic cooperation of the binary or ternary systems when used in minor proportions in various compositions, especially germicidal detergent and soap compositions and the discovery that this synergistic phenomena occurs even at the high pH conditions existing in soap and other detergent formulations.

Relatively small amounts of either the binary or ternary system are sufficient for the increased germicidal effect. Satisfactory results can be obtained when the weight of the binary or ternary composition is from 0.075 to 2.0% of the total weight of the composition. A preferred range is in the weight concentration of about 0.75 to about 1.25% and an excellent product is one containing about 1.0% of the synergistic composition. It should be understood that even concentrations below the ranges set out above will provide some degree of germicidal effect while a higher concentration than those referred to will also give satisfactory results although economic considerations will generally limit the concentration of germicidal composition in a particular medium.

When the binary mixture is considered, the ratio of 3,5-dimethyl-4-chlorophenol to the other component can be in the range of from 1:9 to 9:1, more usually in a ratio of from 1:4 to 4:1, with a ratio of about 1:1 being particularly preferred.

When the ternary system is used, each component can be present in an amount of from 15 to about 50% by weight, preferably from about 25 to 35% by weight. The use of equal amounts by weight of each of the three components is especially preferred.

As has been indicated, the synergistic germicidal compositions described above are useful in soap, which refers to the water-soluble ammonium, metallic or organic base salts of various fatty acids, which are chiefly lauric, oleic, stearic and palmitic acids. The term is intended additionally to cover those products in which soap is a major constituent such as bar, flake, powder, soft and liquid soaps, shaving creams, cleansing cream and the like. The term soap is additionally intended to include the so-called "neutrogenous" soaps which possess the property of being capable of neutralizing a substantial quantity of an acid and of a base without its foaming power and its pH being affected. Such soaps are described in U.S. Pat. No. 2,820,768, (which issued Jan. 21, 1958 on application of Louis E. G. H. Fromont) the teaching of which is incorporated herein by reference.

The germicidal synergistic compositions can further be used with both anionic and nonionic type synthetic detergents. The anionic type synthetics suitable for use in the invention can be described as those detergents having pronounced cleansing power and including in their molecular structure an alkyl radical containing from 6 to 18 carbon atoms and a sulfonic acid or sulfuric acid ester radical. Either organic base, ammonium, sodium or potassium salts of the anionic type detergents can be used. The main types of detergents falling within this category are alkyl-aryl sulfonates, such as sodium or potassium dodecyl benzene sulfonate, sodium or potassium octadecyl benzene sulfonate, and sodium or potassium octyl naphthalene sulfonate; the alkyl sulfates, such as sodium or potassium salts of dodecyl, hexadecyl, and octadecyl sulfates; the sulfonated fatty acid amides, such as sodium or potassium salts of the oleic acid amide of methyl taurine; and the sulfonated monoglycerides such as the mono-coconut oil fatty acid ester of sodium 1,2-hydroxypropane-3-sulfonate.

The nonionic type synthetic detergents suitable for use in the invention may be described as those detergents which do not ionize in solution but owe their water-solubility to un-ionized polar groups such as hydroxy or other linkages. The main types of detergents falling within this category are the polyoxyethylene ethers of the higher fatty alcohols and alkyl phenols; the polyethylene glycols of fatty acids; fatty alkylol amide condensation products; polymers of ethylene and propylene oxides; compounds formed by the addition of propylene oxide to ethylene diamide, followed by the addition of ethylene oxide; fatty acid ethylene oxide condensation products, condensation products of ethylene oxide and a fatty acid ester of a polyhydric alcohol or sugar; and the detergents prepared by heating together a higher fatty acid with a diethanol amine. Some examples of synthetic nonionics suitable for the purposes of this invention are ethylene oxide-tall oil fatty acid reaction products; isooctyl phenol-ethylene oxide reaction products; propylene oxide-ethylene oxide reaction products; and combinations of isooctyl phenolethylene oxide with coconut oil fatty acid ethylene oxide reaction products.

A useful method for evaluating the effectiveness of surgical scrub soaps is the quantitative culturing of bacteria from glove "juice". This method of counting bacteria from the glove has been used to investigate various parameters of the surgeon's scrubbing techniques.

One method of enumerating total bacterial levels on the surfaces of hands was described in 1960 by Lowbury and Lilly in *The British Medical Journal*. They cultured bacteria remaining inside a surgical glove by pouring 100 ml of Ringer's solution into the glove and subculturing a 5 ml aliquot thereof. In 1961, Kundsin and Walter in *Bacteriological Proceedings*, described the culture of sweat accumulated inside surgeon's gloves. Again, in 1961, Stuffard in *The British Medical Journal* (Feb. 25, 1961) obtained counts from the hands of surgeons by suspending reversed gloves by the cuffs in jars containing 100 ml of aqueous 5% serum and plating an aliquot from this.

The glove "juice" technique in conjunction with the principles of synergism testing was used to evaluate the compositions described and claimed herein for synergistic activity in vivo.

One week prior to testing, a panel of at least 18 subjects was placed on a strictly regimented hand-washing schedule. They were prohibited from using all topical medicated preparations, as well as hand lotions and hand creams, for the duration of the test. They were given unmedicated soap for use at home and were allowed to wash as they usually do. They were instructed to report to the testing laboratory daily in the afternoon where they washed both hands with unmedicated soap for a period of one minute. During this control week, the effect of medicated soaps and lotions previously used diminished and the bacterial level on the hands returned to normal.

At the end of the control week, the panel was randomly split into three equal groups of six panelists each. Each germicidal scrub formulation was evaluated on no fewer than six individuals. Each group was successively used to test the various formulations and, in this way, five formulations per week were tested. Washing and bacterial sampling were scheduled in the afternoon; material preparation, plate counts and calculations were done the following morning. When a group was not evaluating a test formulation, it was retained on the control regimen. Using this schedule, the groups were retained on control regimen for at least three days before testing a germicidal formulation. By this time, the effect of a previous test had worn off.

On the test day, each subject of the test group was assigned a specific time to report to the testing laboratory. He was instructed to refrain from washing his hands for a period of one hour prior to reporting. Under supervision, he washed his hands up to and including the wrist with a measured quantity (3.0 ml.) of test formulation for 2 minutes. He then rinsed thoroughly in warm, running tap water and tamped his hands dry with a paper towel. The subject then placed a sterile surgical glove on each hand. A bacterial count was taken on one hand immediately. The subject wore the other glove for exactly 1 hour, during which his activities were not restricted. A count was taken on the other hand exactly 1 hour later.

The bacterial counts on the hands were taken using the "glove juice" technique. The following buffered suspending solution was used to dislodge the bacteria from the hands and to disperse the bacterial clusters.

| SUSPENDING SOLUTION | | |
|---|---|---|
| INGREDIENT | | GRAMS/LITER |
| $KH_2 PO_4$ | | 0.4 |
| $Na_2 HPO_4$ | | 10.1 |
| TRYTON X-100* | | 1.0 |
| DISTILLED WATER | q.s. | 1 Liter |
| | pH | 7.9 |

*Product of Rohm and Haas Co.

A volume of 100 ml of this fluid was poured into the glove while still on the hand of the subject. The glove was secured at the wrist and the subject's hand massaged for 1 minute. A 10 ml aliquot was withdrawn and diluted with 90 ml of sterile nutrient broth containing 1% Tween-80 (product of ICI America Inc.) as a blocking agent for the germicidal agents. Two 1:100 serial dilutions were then made and 1 ml aliquot plated in nutrient agar containing 1% Tween-80 using the pour plate technique. The plates were incubated at 37°C for 18 to 24 hours. Colonies were counted and total viable cells per hand calculated. Using this procedure, viable cell counts usually ranged between $10^4$ and $10^6$ total bacterial cells per washed hand.

Per cent reductions in total viable cells per hand, over a period of one hour, were calculated for each subject by comparing the count taken immediately after washing to the count taken 1 hour later. Per cent reductions for the subjects in the test group were then averaged to arrive at a value for each test formulation. The results are summarized in Table I, below.

TABLE I

| Test Mixtures | (I) Theoretical Additive Effect % Reduction | II Actual Effect % Reduction | (II-I) Increase in Effect |
|---|---|---|---|
| A. 0.5% ii + 0.5% i | 46.9 | 50.5 | 3.6 |
| B. 0.5% iv + 0.5% i | 44.6 | 54.6 | 10.0 |
| C. 0.5% iii + 0.5% i | 30.0 | 46.4 | 16.4 |
| D. 0.33% iv + 0.33% iii + 0.33% i | 40.8 | 70.4 | 29.6 |
| E. 0.33% ii + 0.33% iii + 0.33% i | 42.3 | 68.8 | 26.5 |
| F. 0.33% ii + 0.33% iii + 0.33% iv | 54.0 | 68.3 | 14.2 |
| G. 0.33% ii + 0.33% iv + 0.33% i | 52.0 | 61.3 | 9.3 | i = 3,5-dimethyl-4-chlorophenol
ii = bis-(3,5,6-trichloro-2-hydroxyphenyl) methane
iii = 2,4,4'-trichloro-2'-hydroxydiphenyl ether
iv = 3,4',5-tribromo salicylanilide In evaluating the results obtained, it should be noted that the reductions were not based on a comparison before and after a wash, but on a comparison of results obtained immediately after a wash to those obtained 1 hour later. Results are based on a single application. This test is considered very stringent for soap and/or detergent germicides because they normally function by building up on the skin upon repeated application.

It can be seen that all of the mixtures upon actual testing showed varying degrees of increases in effectiveness compared to their theoretical additive effect. The ternary mixture comprising equal parts of 3,4'-5-tribromosalicylanilide, 2,4,4'-trichloro-2'-hydroxydiphenyl ether and 3,5-dimethyl-4-chlorophenol (test mixture D) shows an increase from the theoretical additive effect of 40% reduction to an actual effect of 70.4% reduction. This mixture not only demonstrated activity greater than the additive effect of its components, it also demonstrated activity considerably greater than the highest effect of any of its components tested separately at the same concentration.

One important parameter respecting surgical scrub preparations and germicidal soap bars is the ability to steadily reduce the bacterial load on the skin over a short period of time. While the activity demonstrated by these types of products after several days or weeks of use is of substantial importance, their ability to continue to reduce bacteria during 1 or 2 hours following a single wash is also an important factor. Surgeons, irrespective of the original count on their hands, require assurance that the scrub regimen will further reduce skin bacteria during surgery where the risk of glove puncture and subsequent wound infection is high. The compositions described herein demonstrate not only long-term additive reduction, but also demonstrate substantial germicidal activity following a single wash.

What I claim is:

1. A bactericidal composition comprising a mixture of
   i. 3,5-dimethyl-4-chlorophenol with one or two of
   ii. bis-(3,5,6-trichloro-2-hydroxyphenyl)methane,
   iii. 2,4,4'-trichloro-2'-hydroxydiphenyl ether and
   iv. 3,4',5-tribromo-salicylanilide, the ratio of (i) to (ii) – (iv) being about 1:1 for a binary mixture and about 1:1:1 for a ternary mixture.

2. A bacteridical composition according to claim 1 comprising 3,5-dimethyl-4-chlorophenol and bis-(3,5,6-trichloro-2-hydroxyphenyl) methane.

3. A bacteridical composition according to claim 1 comprising 3,5-dimethyl-4-chlorophenol and 2,4,4'-trichloro-2'-hydroxydiphenyl ether.

4. A bacteridical composition according to claim 1 comprising 3,5-dimethyl-4-chlorophenol and 3,4',5-tribromo-salicylanilide.

5. A bacteridical composition according to claim 1 comprising 3,5-dimethyl-4-chlorophenol, bis-(3,5,6-trichloro-2-hydroxyphenyl)methane and 2,4,4'-trichloro-2'-hydroxydiphenyl ether.

6. A bacteridical composition according to claim 1 comprising 3,5-dimethyl-4-chlorophenol, 2,4,4'-trichloro-2'-hydroxydiphenyl ether and 3,4',5-tribromo-salicylanilide.

7. A bacteridical composition according to claim 1 comprising 3,5-dimethyl-4-chlorophenol, bis-(3,5,6-trichloro-2-hydroxyphenyl)methane and 3,4',5-tribromo-salicylanilide 8. The bactericidal composition of claim 1, wherein the mixture of (i) and (ii) – (iv) is 0.075 to 2.0% by weight of the composition which further comprises an anionic or nonionic detergent or mixture thereof.

9. The bactericidal composition of claim 1, wherein the mixture of (i) and (ii) – (iv) is 0.075 to 2.0% by weight of the composition which further comprises a soap.

* * * * *